(12) United States Patent  
Lewis

(10) Patent No.: US 8,111,395 B2
(45) Date of Patent: Feb. 7, 2012

(54) SPECTROMETRIC INVESTIGATION OF HETEROGENEITY

(75) Inventor: E. Neil Lewis, Olney, MD (US)

(73) Assignee: Malvern Instruments Ltd, Malvern (GB)

( * ) Notice: Subject to any disclaimer, the term of this patent is extended or adjusted under 35 U.S.C. 154(b) by 0 days.

(21) Appl. No.: 12/006,677

(22) Filed: Jan. 4, 2008

(65) Prior Publication Data

US 2008/0180660 A1    Jul. 31, 2008

Related U.S. Application Data

(60) Provisional application No. 60/879,306, filed on Jan. 5, 2007, provisional application No. 60/958,337, filed on Jul. 5, 2007.

(51) Int. Cl.
*G01J 3/28* (2006.01)
(52) U.S. Cl. ........................................ 356/326; 356/328
(58) Field of Classification Search .................. 356/326, 356/328
See application file for complete search history.

(56) References Cited

U.S. PATENT DOCUMENTS

| 5,991,470 A * | 11/1999 | Swithers et al. .............. 382/322 |
| 6,002,476 A | 12/1999 | Treado |
| 6,037,772 A | 3/2000 | Karczmar et al. |
| 6,067,154 A | 5/2000 | Hossain |
| 6,288,782 B1 | 9/2001 | Worster |
| 6,545,755 B1 | 4/2003 | Ishihama |
| 7,061,606 B2 | 6/2006 | Treado et al. |
| 7,532,320 B2 | 5/2009 | Neiss |
| 7,595,878 B2 | 9/2009 | Nelson |
| 2005/0179899 A1 * | 8/2005 | Palti-Wasserman et al. . 356/417 |
| 2005/0277816 A1 | 12/2005 | Maier |
| 2006/0063989 A1 | 3/2006 | Hogan |
| 2006/0170916 A1 | 8/2006 | Voigt |
| 2007/0127022 A1 * | 6/2007 | Cohen et al. .................. 356/326 |
| 2008/0084553 A1 | 4/2008 | Neiss |

FOREIGN PATENT DOCUMENTS

WO    WO0122060    8/2000

OTHER PUBLICATIONS

U.S. Appl. No. 10/088,008, filed Aug. 15, 2000, Valet.

* cited by examiner

*Primary Examiner* — Tarifur Chowdhury
*Assistant Examiner* — Abdullahi Nur
(74) *Attorney, Agent, or Firm* — Kristofer E. Elbing

(57) ABSTRACT

In one general aspect, a spectroscopic apparatus is disclosed for investigating heterogeneity of a sample area. The apparatus includes an image acquisition system operative to acquire images of a plurality of sub-areas in the sample area and a sub-area selection interface operative to receive a selection designating one of the sub-areas for which an image has been obtained. A spectrometer has a field of view and is operative to acquire a spectrum of at least part of one of the sub-areas in its field of view, and a positioning mechanism is responsive to the sub-area selection interface and operative to position the field of view of the spectrometer relative to the sample area based on a received selection.

29 Claims, 20 Drawing Sheets

SPECTROMETRIC INVESTIGATION OF HETEROGENEITY

CROSS-REFERENCE TO RELATED APPLICATIONS

This application claims the benefit under 35 U.S.C. 119(e) of United States provisional application entitled SPECTROMETRIC INVESTIGATION OF HETEROGENEITY, filed Jan. 5, 2007 (Ser. No. 60/879,306), and United States provisional application entitled SPECTROMETRIC INVESTIGATION OF PHARMACEUTICAL HETEROGENEITY, filed Jul. 5, 2007 (Ser. No. 60/958,337), both of which are herein incorporated by reference.

FIELD OF THE INVENTION

This invention pertains to instrumentation, including particle image analyzers with spectrometric capabilities.

BACKGROUND OF THE INVENTION

Particle image analyzers are well-known instruments that can use image analysis techniques to allow users to automatically acquire and analyze images of a large number of particles. These instruments can then provide statistical information about the size and shape of particles. FIG. 1 shows one example of such a system, the Morphologi® Particle Image Analyzer available from Malvern Instruments, Inc. of Malvern UK. This system is described in a section of the specification of this document.

Spectral imaging techniques have also been applied to the analysis of large numbers of particles. These systems can provide statistical information about the distribution of chemical species in the particles. Systems of this type are described in more detail in US published application no 20060282223, which is herein incorporated by reference.

SUMMARY OF THE INVENTION

Several aspects of the invention are presented in this application. In one general aspect, the invention features a spectroscopic apparatus for investigating heterogeneity of a sample area. The apparatus includes an image acquisition system operative to acquire images of a plurality of sub-areas in the sample area and a sub-area selection interface operative to receive a selection designating one of the sub-areas for which an image has been obtained. A spectrometer has a field of view and is operative to acquire a spectrum of at least part of one of the sub-areas in its field of view, and a positioning mechanism is responsive to the sub-area selection interface and operative to position the field of view of the spectrometer relative to the sample area based on a received selection.

In preferred embodiments, the positioning mechanism can include electromechanical elements. The positioning mechanism can include an x-y stage responsive to x-y coordinate information from the sub-area selection interface. The sub-area selection interface can be responsive to direct selection of a sub-area by a user. The apparatus can further include analysis logic operative to analyze the images acquired by the image acquisition system. The sub-area selection interface can be responsive to the analysis logic to select sub-areas having predetermined characteristics. The sub-area selection interface can be responsive to the analysis logic to select sub-areas having predetermined morphological characteristics. The sub-area selection interface can be responsive to the analysis logic to select sub-areas having predetermined color characteristics. The analysis logic can include statistical analysis logic, sorting logic, and/or contaminant detection logic. The spectrometer can be an infrared spectrometer. The spectrometer can be a Raman spectrometer. The area can be an area of dispersed particles with the sub-areas being individual particles in the area of dispersed particles. The image acquisition system can operate in the visible range. The apparatus can further include a mapping module responsive to the image acquisition system and to the spectrometer and operative to create a map that presents spectral information for each of the sub-areas from the spectrometer at a location from which it was received. The mapping module can be operative to superimpose the spectral information onto an image from the image acquisition system. The mapping module can map point measurement values to larger areas having matching physical characteristics. The mapping module can also be operative to indicate statistical properties of mapped areas.

In another general aspect, the invention features a spectroscopic method for investigating heterogeneity of a sample area that includes acquiring images of a plurality of sub-areas in the sample area using an image acquisition system, receiving a selection of one of the sub-areas for which an image has been obtained, positioning a field of view of a spectrometer relative to the sample area so as to place at least part of the selected sub-area in the field of view, and acquiring a spectrum of the selected sub-area.

In preferred embodiments, the method can further include the step of mapping spectral information from the spectrometer to a location from which it was received. The method can further include the steps of deriving physical information about the one of the sub-areas, and setting a spectral range of the step of acquiring in response to the physical information.

In a further general aspect, the invention features a spectroscopic apparatus for investigating heterogeneity of a sample area that includes means for acquiring images of a plurality of sub-areas in a sample, means for receiving a selection of one of the sub-areas for which an image has been obtained, means for positioning a field of view of a spectrometer relative to the sample area so as to place at least part of the selected sub-area in the field of view, and means for acquiring a spectrum of the selected sub-area.

In another general aspect, the invention features a spectroscopic method for investigating heterogeneity of a sample area that includes receiving spatial information for a plurality of sub-areas in a sample area, receiving separate spectral information items for each of the plurality of sub areas, wherein a selection of the separate spectral information items is based on the spatial information, and combining the spatial information with the spectral information to create a map showing spatial distribution of spectral information for the sample area.

In preferred embodiments, the method can further include the step of acquiring the spatial information by a preliminary imaging system and the step of acquiring the spectral information by a spectrometer that is responsive to automatically generated identification information derived from the spatial information acquired in the step of acquiring.

In a further general aspect, the invention features a spectroscopic apparatus for investigating heterogeneity of a sample area that includes means for receiving spatial information for a plurality of sub-areas in a sample area, means for receiving separate spectral information items for each of the plurality of sub areas, wherein a selection of the separate spectral information items is based on the spatial information, and means for combining the spatial information with the spectral information to create a map showing spatial distribution of spectral information for the sample area.

In another general aspect, the invention features an apparatus for investigating heterogeneity of a sample area that includes an image acquisition system operative to acquire images of a plurality of sub-areas in the sample area, a sub-area selection interface operative to automatically select one of the sub-areas for which an image has been obtained based on its color, and quantitative analysis logic operative to perform a quantitative analysis on image data from one or more of the sub-areas. In preferred embodiments, the sub-area selection interface can be operative to automatically select one of the sub-areas for which an image has been obtained based on a color that corresponds to a predetermined stain.

In a further general aspect, the invention features a method for investigating heterogeneity of a sample area that includes acquiring images of a plurality of sub-areas in the sample area, automatically selecting one of the sub-areas for which an image has been obtained based on its color, and performing a quantitative analysis on image data from one or more of the sub-areas.

In another general aspect, the invention features an apparatus for investigating heterogeneity of a sample area that includes means for acquiring images of a plurality of sub-areas in the sample area, means for automatically selecting one of the sub-areas for which an image has been obtained based on its color, and means for performing a quantitative analysis on image data from one or more of the sub-areas.

Systems according to the invention can be advantageous in that they allow for spectrometric imaging and screening without the expense and time that may be required by array-based infrared chemical imaging systems.

DESCRIPTION OF AN ILLUSTRATIVE EMBODIMENT

Figure 2:
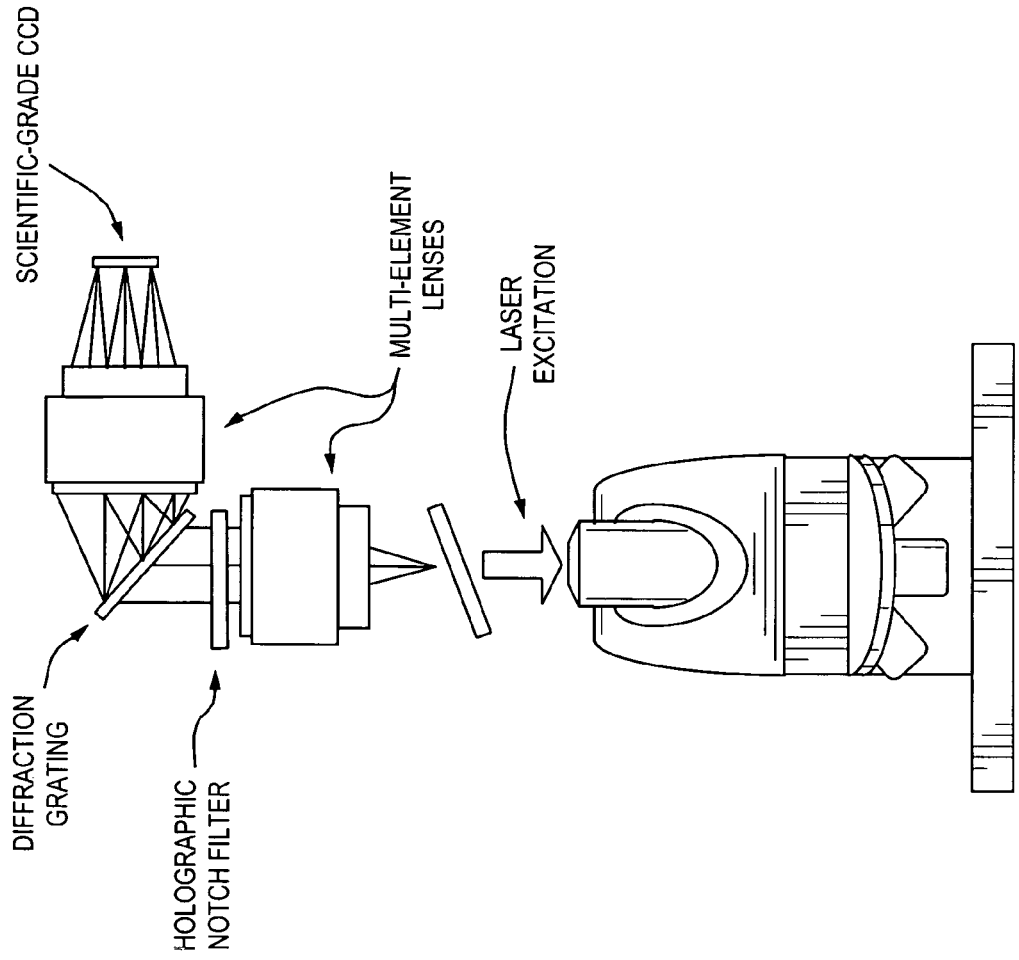
FIG. 2 is an image of a system according to the invention employing the analyzer of FIG. 1.
Figure 1:
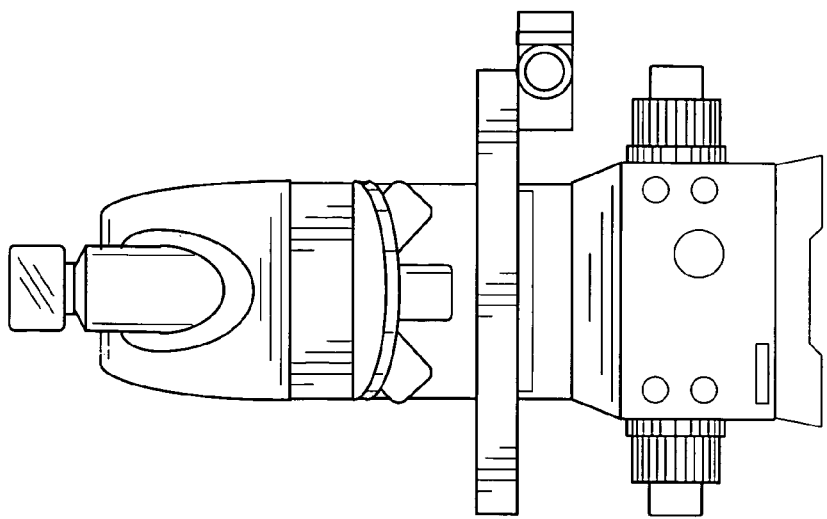
FIG. 1 is an image of a prior art particle image analyzer.

Referring to FIG. 2, an illustrative system 10 according to the invention includes a spectrometer 22 in addition to the microscope body 12, x-y stage 14, and camera 16. The spectrometer can use the same microscope optics as the camera either by swapping them or using an optical switch to alternate between them. In Raman implementations, a laser source can also pass its beam through the same optics, such as through the use of a beam splitter 24.

Results from the camera and computer are also preferably analyzed and presented on a same computer (e.g., a PC workstation). The principles of the invention can be applied to a variety of types of apparatuses, methods, and applications. For example, a system employing macroscopic optics could be used instead of microscopic optics. The camera could acquire its images in a variety of ways, such as by using a Charge Coupled Device (CCD) to acquire grayscale or color images in the visible wavelength range. These apparatuses can also employ any type of spectrometric detection, such as methods based on gratings or interference. And while the illustrative embodiment uses NIR spectrometry, other types of spectrometry could be used as well, such as mid-infrared spectrometry, Raman spectrometry, or fluorescence spectrometry.

Figure 3A:
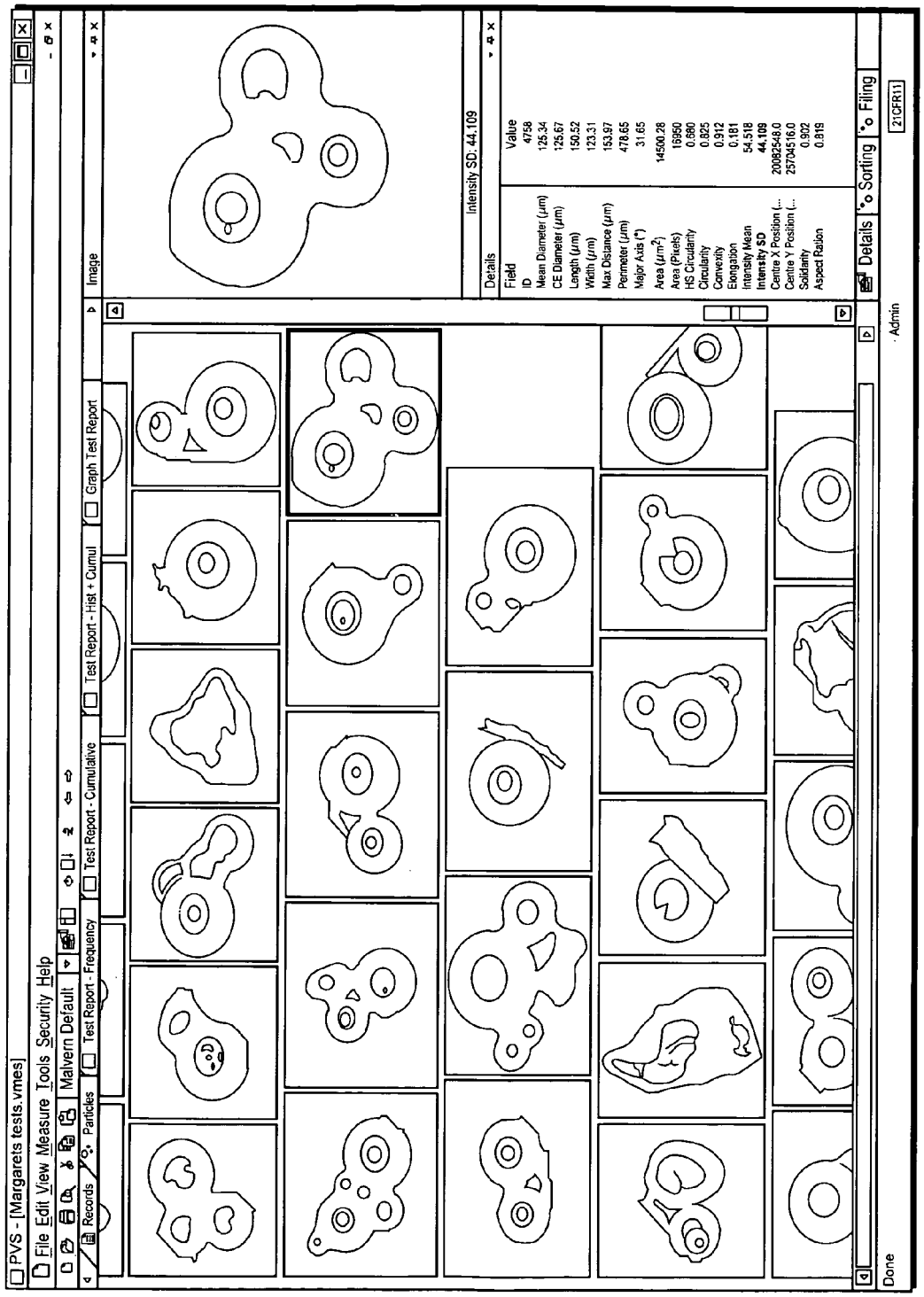
FIG. 3A is an illustration of a screen shot particle record view that can be provided by the system of FIG. 2 for a first type of particle in an illustrative sample.
Figure 3B:
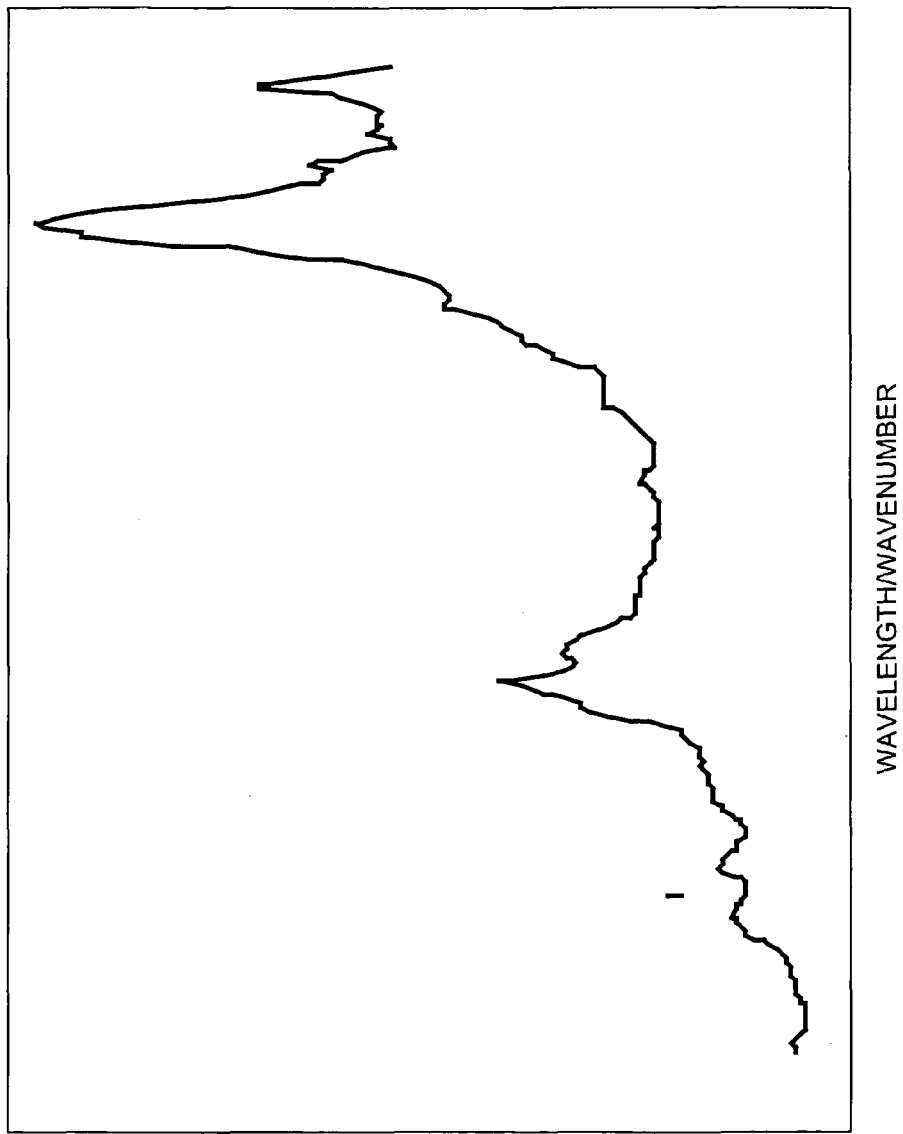
FIG. 3B is a spectrum for one of the particles shown in the screen shot of FIG. 3A, which can be provided by the system of FIG. 2.

In operation, referring to FIG. 3A, the system first acquires a visible image of a sample area, such as a dry dispersion of particles from a pharmaceutical raw material. The system can then provide the user a series of images of individual particles. This can allow the user to select one of the particles and then cause the system to obtain a spectrum of that particle by moving the x-y to position the selected particle in a field of view of the spectrometer (see FIG. 3B). Note that other types of mechanisms for moving the sample relative to the spectrometer's field of view are possible, such as by moving mirrors, or even moving the spectrometer itself. Some can also operate passively, such as by gravity or convection. The field of view of the spectrometer is preferably smaller than the size of a particle.

Figure 4A:
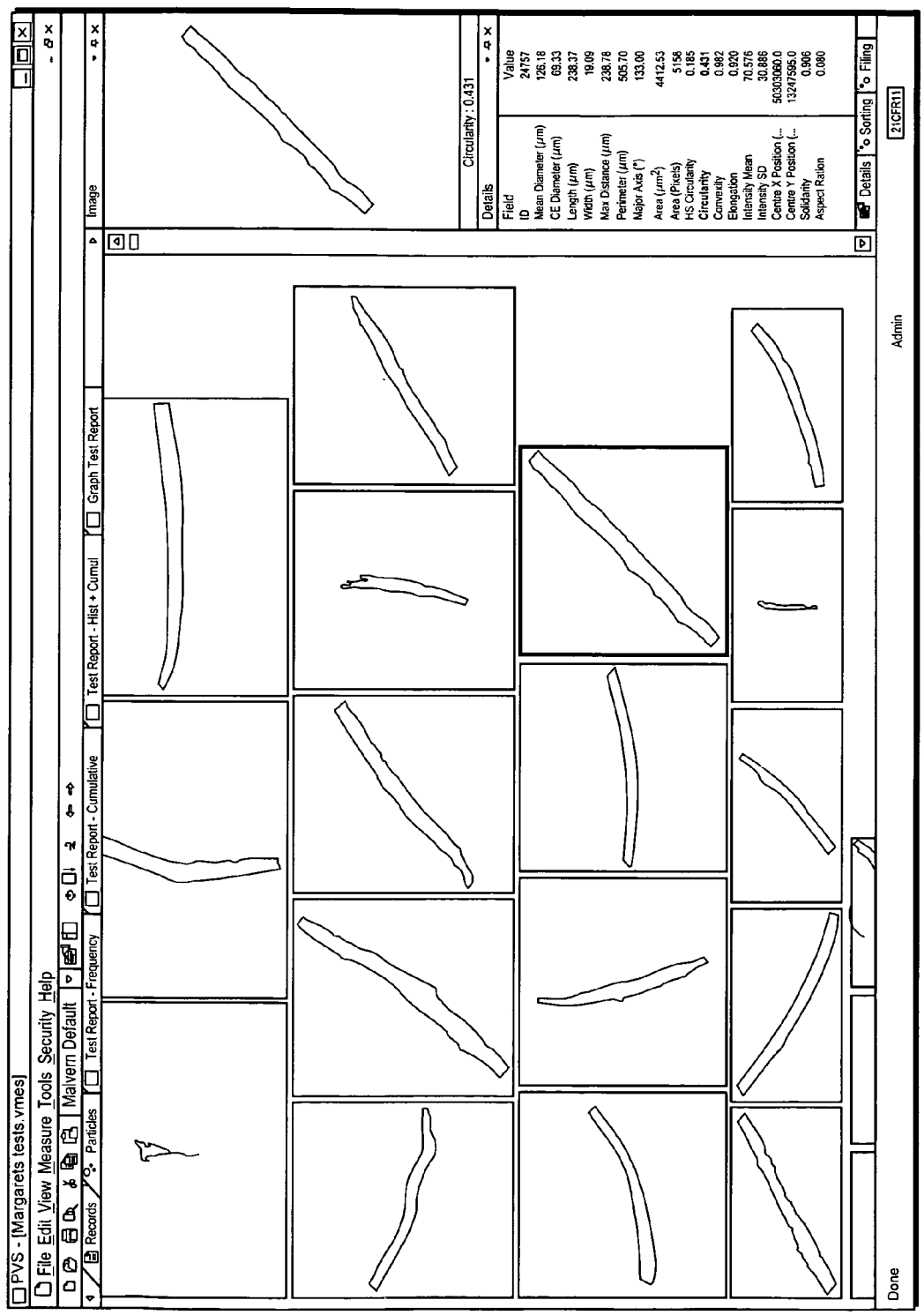
FIG. 4A is an illustration of a screen shot particle record view that can be provided by the system of FIG. 2 for a second type of particle in an illustrative sample.
Figure 4B:
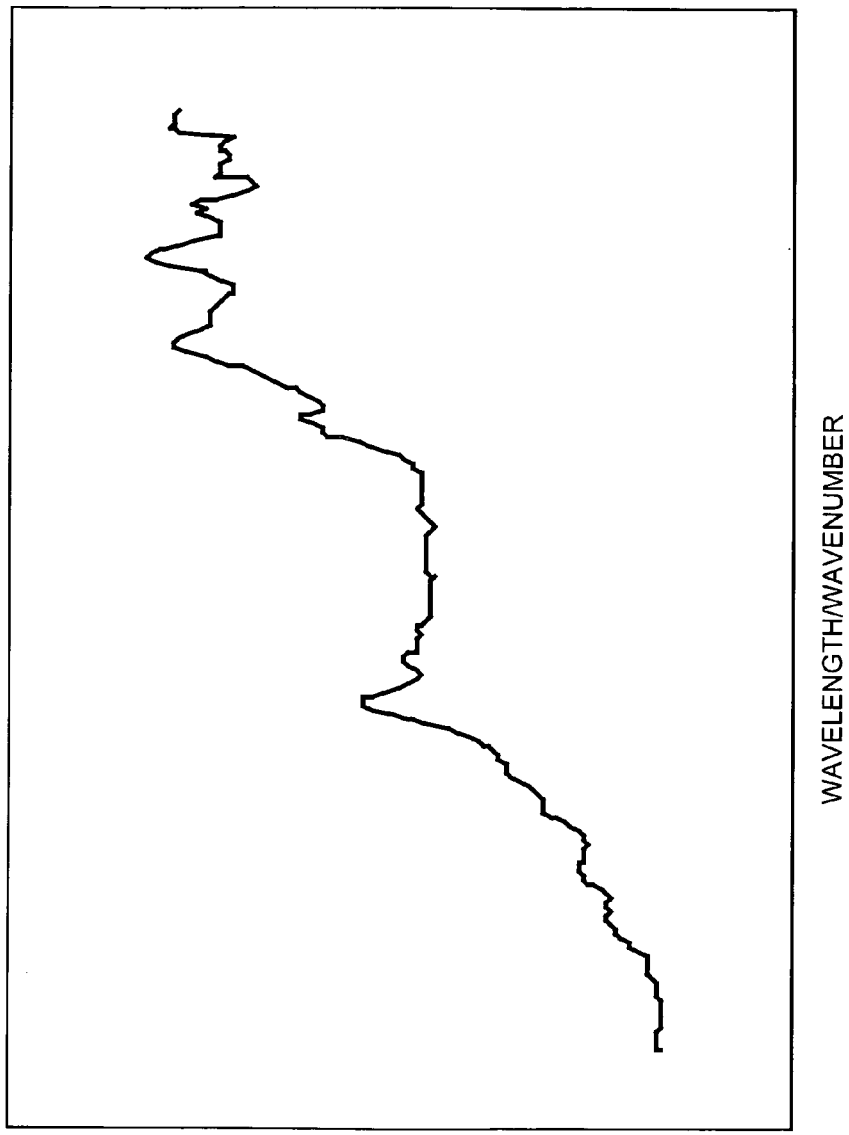
FIG. 4B is a spectrum for one of the particles shown in the screen shot of FIG. 4A, which can be provided by the system of FIG. 2.

The system can also select particles automatically. Results of statistical or other types of image or numerical analysis can be used to determine which particles to select based on morphological differences. For example, the smallest, largest, most spherical, darkest, or lightest particles could be selected automatically (e.g., compare FIGS. 3A and 3B with FIGS. 4A and 4B). Combinations of morphological, physical, calorimetric, or other attributes could be used as well.

The system can also be applied to other types of samples, such as coarse or fine particulates and heterogeneous liquids or surfaces. More specific examples can include items such as manufactured products, seeds, cattle feed, biological cells or other bounded biological entities such as spores, organelles, or bacteria. Other types of operations can also be applied to selected areas by the system. A particle could be mechanically extracted for disposal or further processing, for example.

Figure 5:
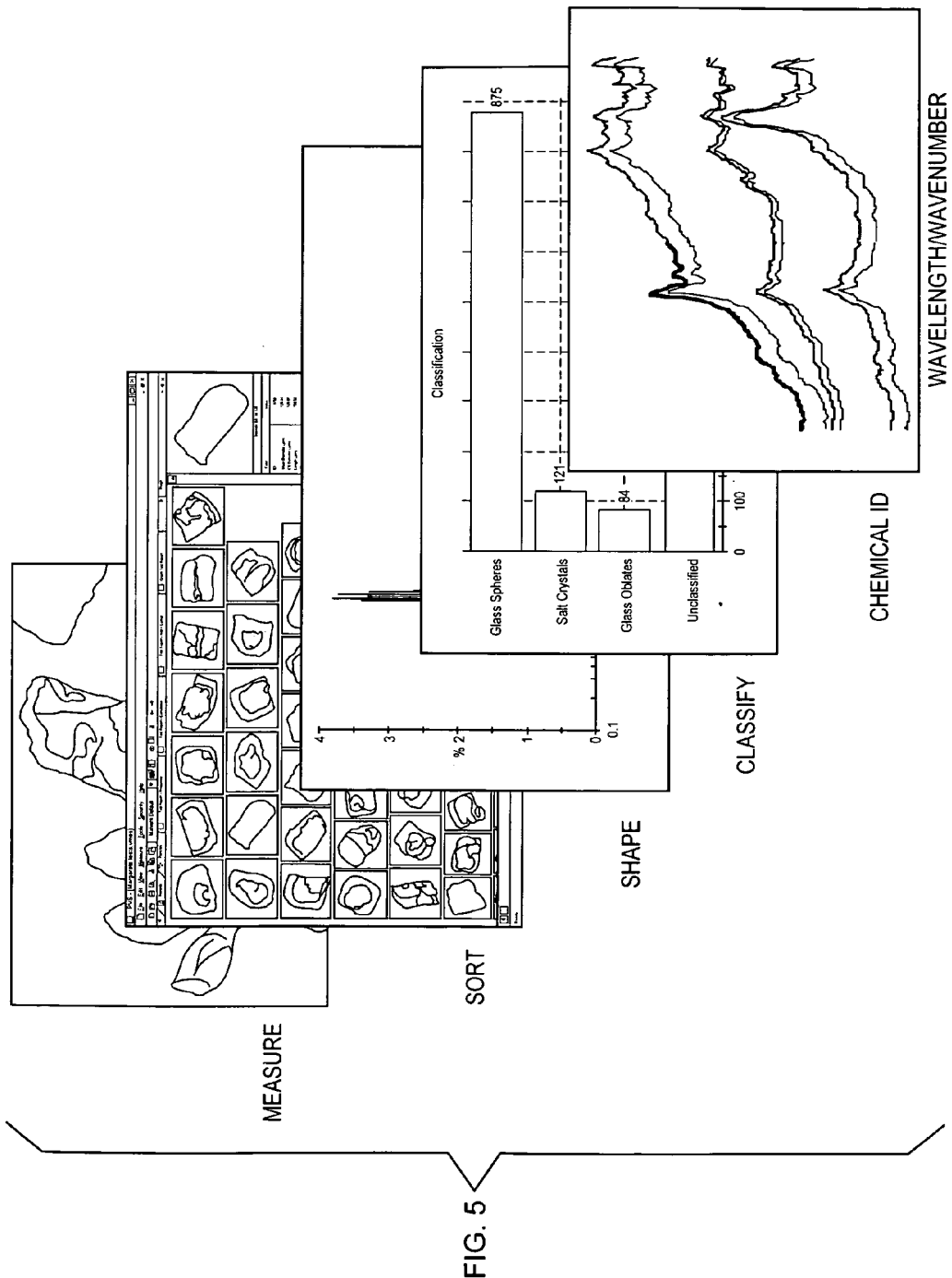
FIG. 5 is a series of images illustrating a sequence of screen shots that can be produced by the system of FIG. 2 for an illustrative sample.
Figure 6A:
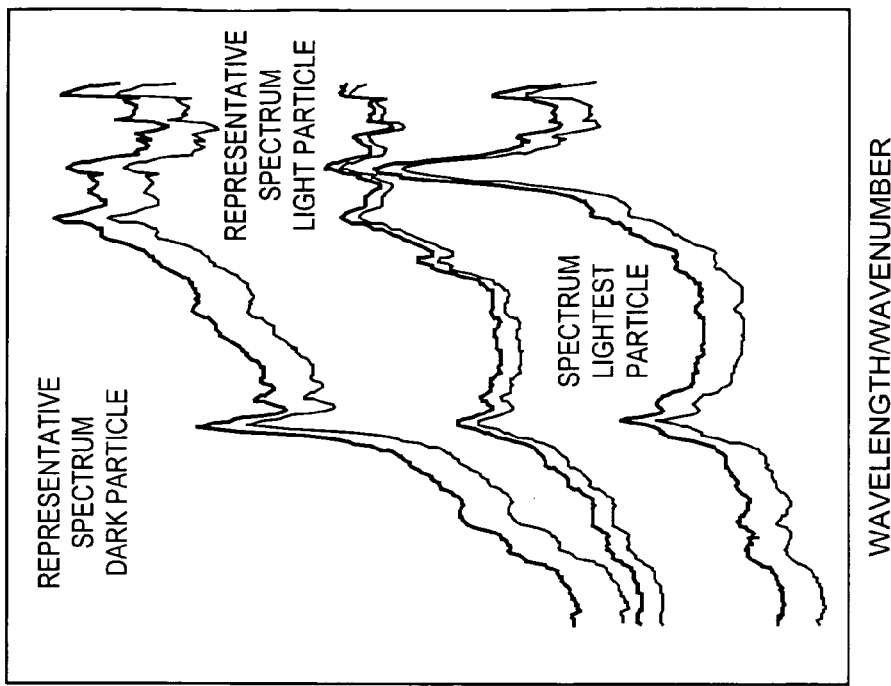
FIG. 6A is a series of selected images of samples from an illustrative sample for use with the system of FIG. 2.
Figure 6B:
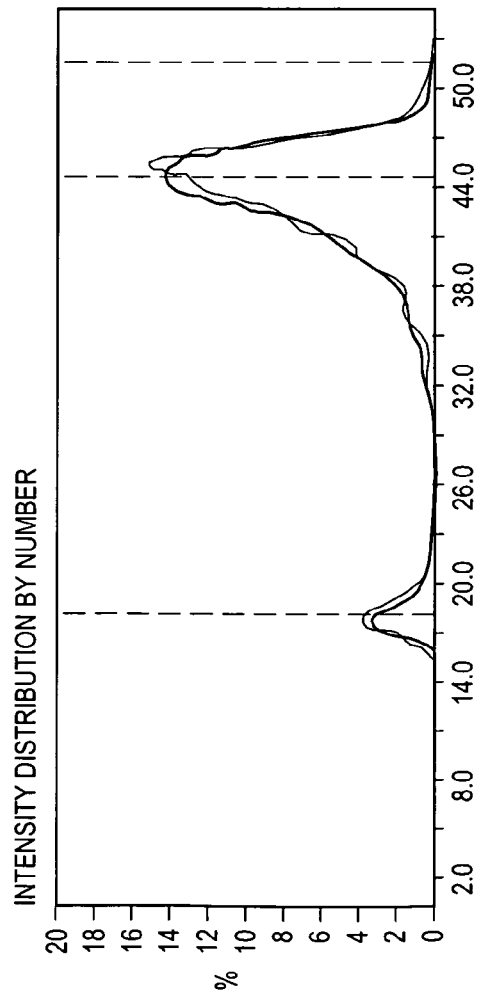
FIG. 6B is a graph illustrating the intensity distribution of transparency in the illustrative sample for FIG. 6A.
Figure 6C:
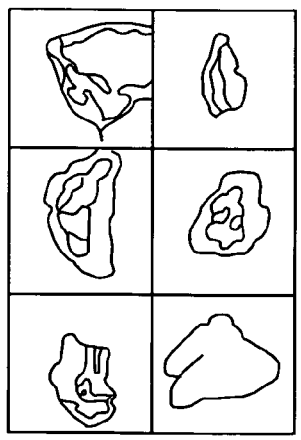
FIG. 6C is a plot showing a family of spectra for different types of samples in the illustrative sample.

Referring to FIGS. 5-6, in one example, particles having different transparencies could be processed by the system. In this example, most particles are semi-transparent and produce low intensity images, while some are darker and result in higher contrast images (see FIG. 6A). As shown in FIG. 6B, statistical processing by the system can reveal that the transparency distribution for this sample has two peaks-one large one for the most common, more transparent, particles and one small one for the less common, darker, particles. The system can then produce one or more spectra for a variety of salient points in this distribution, such as at the centroids of its peaks or their outlying edges (see FIG. 6C). These spectra can then be displayed to the user or compared to known spectra in a spectral library or processed by a variety of multivariate or chemometrics means. These processing operations can derive information about the chemical origin or identification of the selected object or more fundamental information about the molecular or crystal structure.

Figure 7:
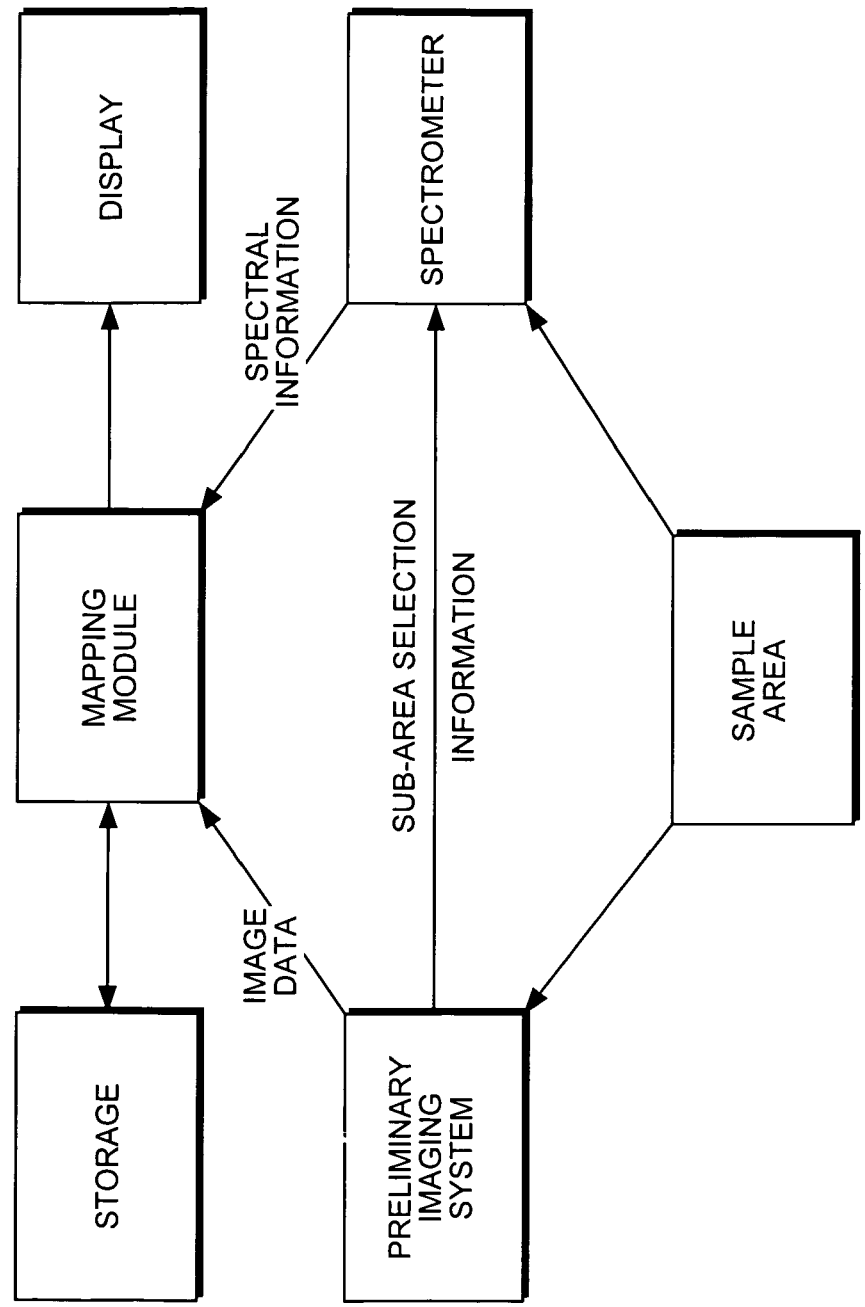
FIG. 7 is a block diagram of a system according to the invention that employs a sparse image information acquisition mode.
Figure 8:
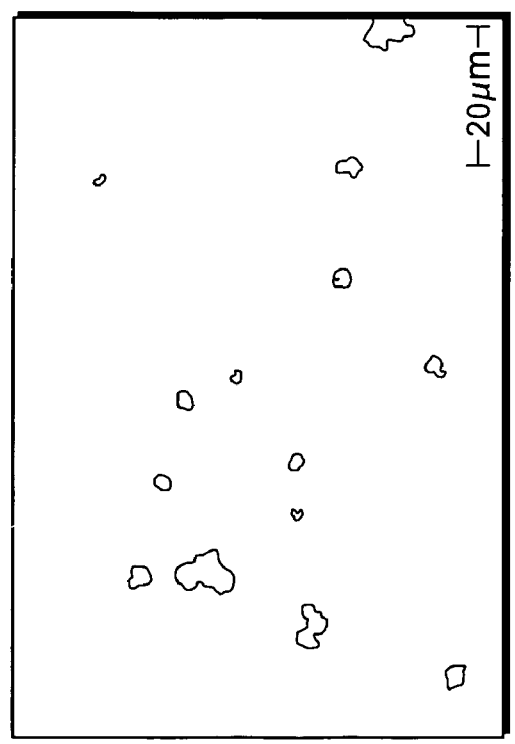
FIG. 8 is an acquired grayscale image of a pharmaceutical formulation with two active ingredients and one inactive ingredient dispersed onto a surface using a standard metered-dose inhaler.

Referring to FIGS. 7-8, systems according to the invention can also use a sparse image information acquisition and/or mapping mode. In this mode, the system can obtain a first image of a sample area in which information of interest is relatively sparse. This image may include a sparse set of entities of interest separated by background space, such as the dispersed pharmaceutical formulation shown in FIG. 8, or it may include any other type of image in which only a small number of image sub-areas are of interest.

Figure 9:
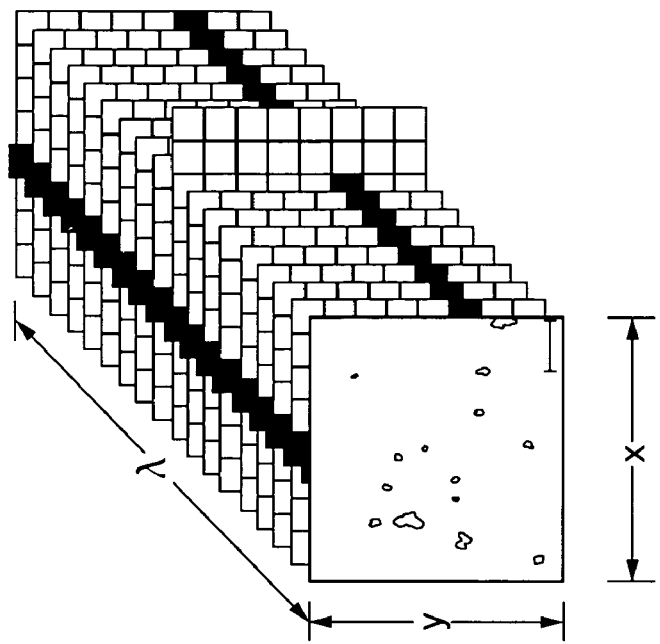
FIG. 9 is a diagram illustrating a blank hypercube data set for the image of FIG. 7.

Referring to FIG. 9, one traditional prior art method of acquiring spectral information for a sample area is to acquire a full spectrum for every point to derive a full spectral hyperspectral data cube for the sample. This data cube includes an x-y image of the sample at each of a series of wavelengths $\lambda$, with a vector v in the wavelength axis corresponding to a single point spectrum. Much effort has been expended to build high-speed imaging spectrometers that can create full hyperspectral data cubes quickly.

Systems according to the invention operate differently. These systems first employ a preliminary imaging detection subsystem to select particles of interest. This step can be automatic or semi-automatic, and can be based on a variety of information about the sample, such as morphology, colorimetry, statistical properties, or pattern recognition. It is also preferably quick and/or inexpensive to perform, because it operates at visible wavelengths, for example. The particles selected by the preliminary imaging subsystem are identified to a spectrometry system, such as in the form of a list of particle centroids communicated electronically.

As in the embodiment presented above in connection with FIG. 2, the system can cause the spectrometer to obtain one or more spectra for each of the particles of interest by moving the position of an x-y stage to the selected particles in a field of view of the spectrometer. Note that other types of mechanisms for moving the sample relative to the spectrometer's field of view are also possible, such as by moving mirrors, or even moving the spectrometer itself. Some can even operate passively, such as by gravity or convection.

Figure 10C:
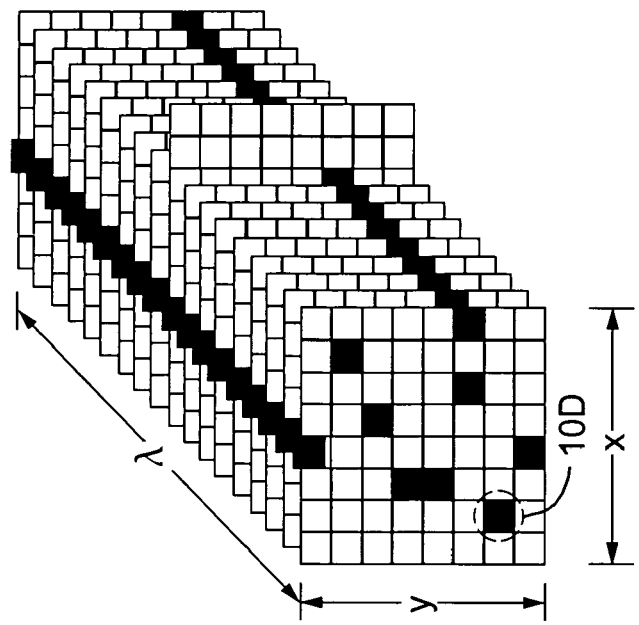
FIG. 10C is a diagram illustrating an enlarged image area from FIG. 10A.
Figure 10D:
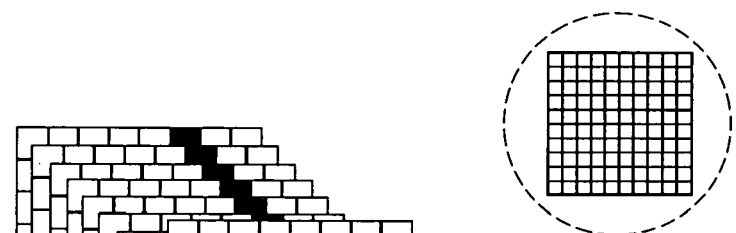
FIG. 10D is a diagram illustrating an enlarged image area from FIG. 10B.
Figure 10A:
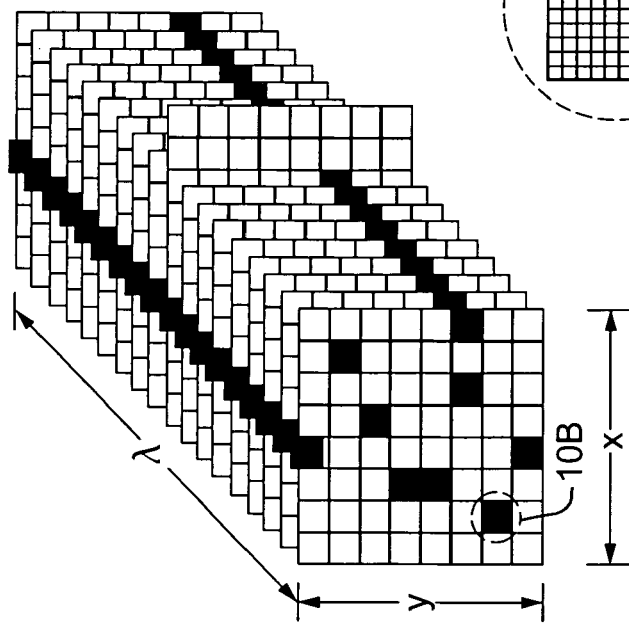
FIG. 10A is a diagram illustrating a populated sparse hypercube data set that employs image areas that each correspond an individual spectrum.
Figure 10B:
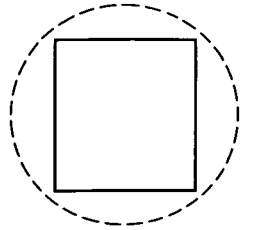
FIG. 10B is a diagram illustrating a populated sparse hypercube data set that employs image areas that each correspond to a plurality of spectra.
Figure 11:
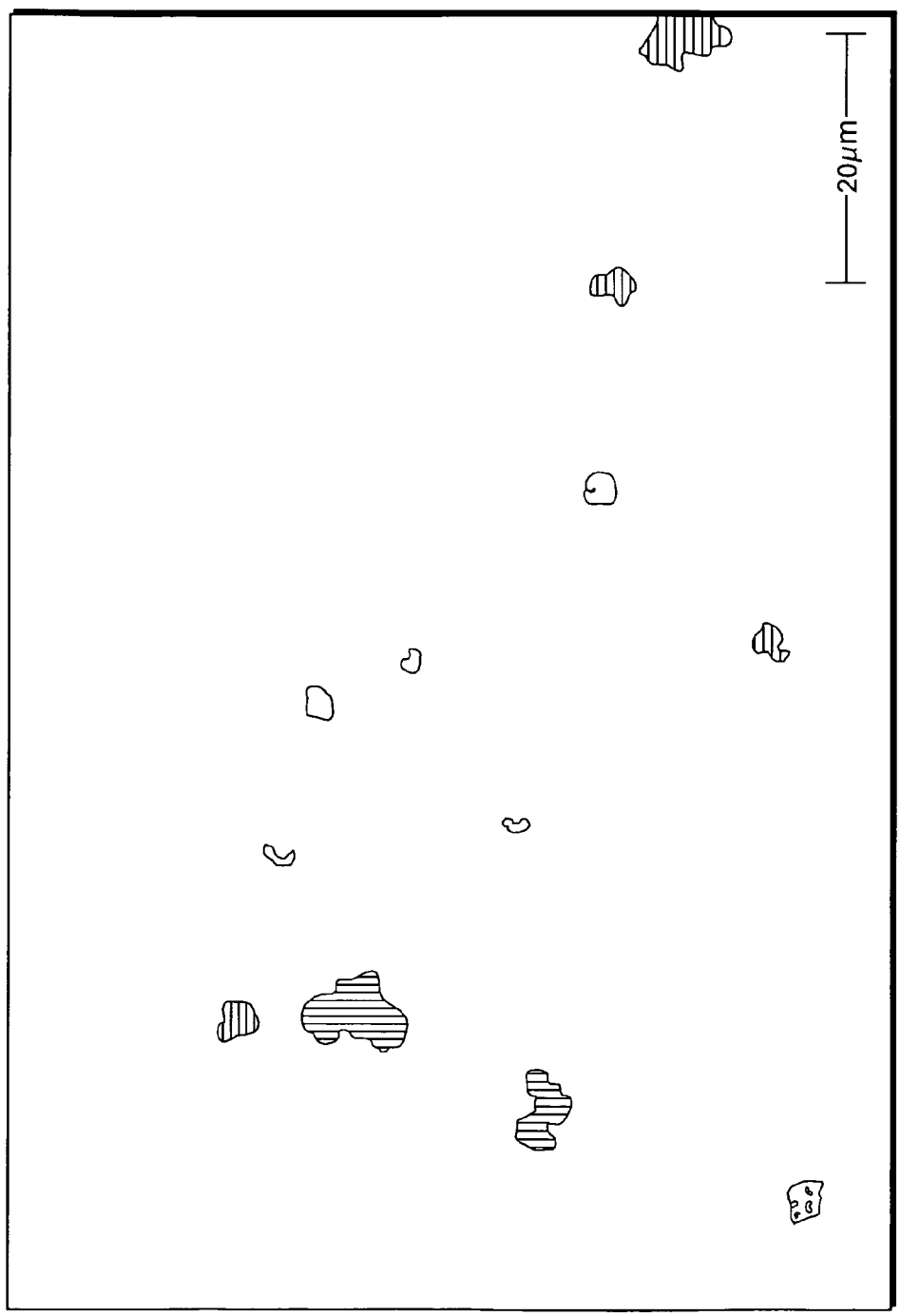
FIG. 11 is a map of the type that can be produced with a system such as the system of FIG. 7 based on the sample for which an acquired image is shown in FIG. 8.

Referring to FIGS. 10A-10B, the values from the spectrometer are mapped to locations in a sparse hyperspectral data cube that correspond to the respective locations of sub-areas of interest, such as particles. This mapping can take a variety of forms, such a single-sample, geometric map, in which each sub-area is represented by a geometrically accurate sub-area shape exhibiting a single representational treatment (e.g., a color or a hatching pattern). Each shape in this type of map corresponds to a single spectral measurement of a single particle, such as one taken at its centroid (see FIG. 10A). And each shape has a perimeter that matches the perimeter of its respective particle and is located in the image at a location that corresponds to its location in the sample area. The result is a map that can resemble a map derived from a full spectral scan of the sample area, but includes little or no data outside the regions of interest. In the case of the pharmaceutical formulation, for example, the different types of particles in the formulation could be mapped to different colors on a white background. Or they could be mapped to different hatching patterns, as shown in FIG. 11.

A multi-sample, geometric map can be used as well, in which each sub-area is actually a small spectral image of the sample with a plurality of pixels each corresponding to one of several differently located spectral measurements for different parts of the sub-area. Multi-sample maps can also display a single treatment for each sub-area, where the treatment is defined by the results of multiple samples (see FIG. 10B). For example, a median wavelength response for a series of measurements taken over different parts of a sub-area could be computed and displayed as a color. Suitable techniques used for obtaining multiple samples for a sub-area, including statistical techniques, are described, for example, in copending application no. 60/860,345, entitled SPECTROMETRIC CHARACTERIZATION OF PHARMACEUTICAL HETEROGENEITY, filed on Nov. 20, 2006, which is herein incorporated by reference.

The system can produce maps in a variety of ways. It may produce them by superimposing results from the spectrometer onto the image produced by the preliminary imaging system, for example, or it may produce them using the results of the preliminary imaging system as a starting point for a mask. They maps can also be produced based only on the location and/or morphology information received from the preliminary imaging system.

The data sets can be stored in a variety of ways. They can be stored in much the same way would be a full hyperspectral data cube, except that non-sampled areas would be represented as empty, such as through the use of an IEEE 754 floating point NaN symbol (Not a Number). They can also be stored in a more compact format to reduce data storage requirements. This format could include a data structure that holds the received spectra and their coordinates, for example, or it could employ one of more of a variety of known data compression methods suitable for encoding sparse data sets, such as Run Length Encoding (RLE). To display a map or image plane from a compactly stored data cube, the system would have to decompress or otherwise reconstruct the map or image.

The maps and data sets may also be spatially compressed. If each sub-area only corresponds to a single measurement, for example, the data could be presented and stored at a much lower resolution that that of the preliminary imaging system. And in some applications, it may be suitable to represent each sub-area with a representation that does not conform to the shape of the sub-areas, such as an individual pixel, or even a symbol. All of the above techniques can permit faster acquisition times, processing times, and/or storage requirements by reducing redundant or unimportant operations and/or spatial data.

The data sets, maps, and spectral measurements may also exhibit spectral sparseness. The selections presented by the preliminary imaging system can define which wavelengths should be used for different sub-areas of a sample area, for example, such as by adjusting an excitation frequency (e.g., selecting a laser frequency) or selecting a sensitivity range for the spectrometer. This approach can further reduce acquisition times, processing times, and/or storage requirements by reducing redundant or unimportant operations and/or spectral data. Once maps have been created, they can be displayed, stored, or serve as the basis for further investigation or processing.

Systems according to the invention can be created using a specially programmed general purpose computer, dedicated hardware, or a combination of both. In one embodiment, the system is based on a Microsoft Windows®-based computer system, but other platforms could be used as well.

Techniques presented in this application such as the sparse acquisition techniques can also be applied to high throughput systems, such as are described in U.S. Pat. No. 6,483,112, entitled HIGH-THROUGHPUT INFRARED SPECTROSCOPY. They may also be applied to high-volume on-line spectroscopic composition testing of manufactured pharmaceutical dosage units such as are described in U.S. Pat. No. 6,690,464, entitled HIGH-VOLUME ON-LINE SPECTROSCOPIC COMPOSITION TESTING OF MANUFACTURED PHARMACEUTICAL DOSAGE UNITS. And they may be applied to HPLC and other techniques described in U.S. application Ser. No. 10/328,713, entitled SPECTROMETRIC PROCESS MONITORING. All of these applications are herein incorporated by reference.

In addition to combining the teachings of this application with the above-referenced documents, it is contemplated that they could also be combined with the teachings of U.S. application Ser. No. 11/499,390, entitled PHARMACEUTICAL MIXTURE EVALUATION, filed on Aug. 4, 2006, U.S. application No. 60/860,345, entitled SPECTROMETRIC CHARACTERIZATION OF PHARMACEUTICAL HETEROGENEITY, filed on Nov. 20, 2006, and U.S. application No. 60/879,306, entitled SPECTROMETRIC INVESTIGATION OF HETEROGENEITY, filed on Jan. 5, 2007. For example, particles could be stained before image acquisition and analysis, and color resulting from staining could be used as a selection parameter. All of these applications are herein incorporated by reference.

Particle Analyzer

Figure 12:
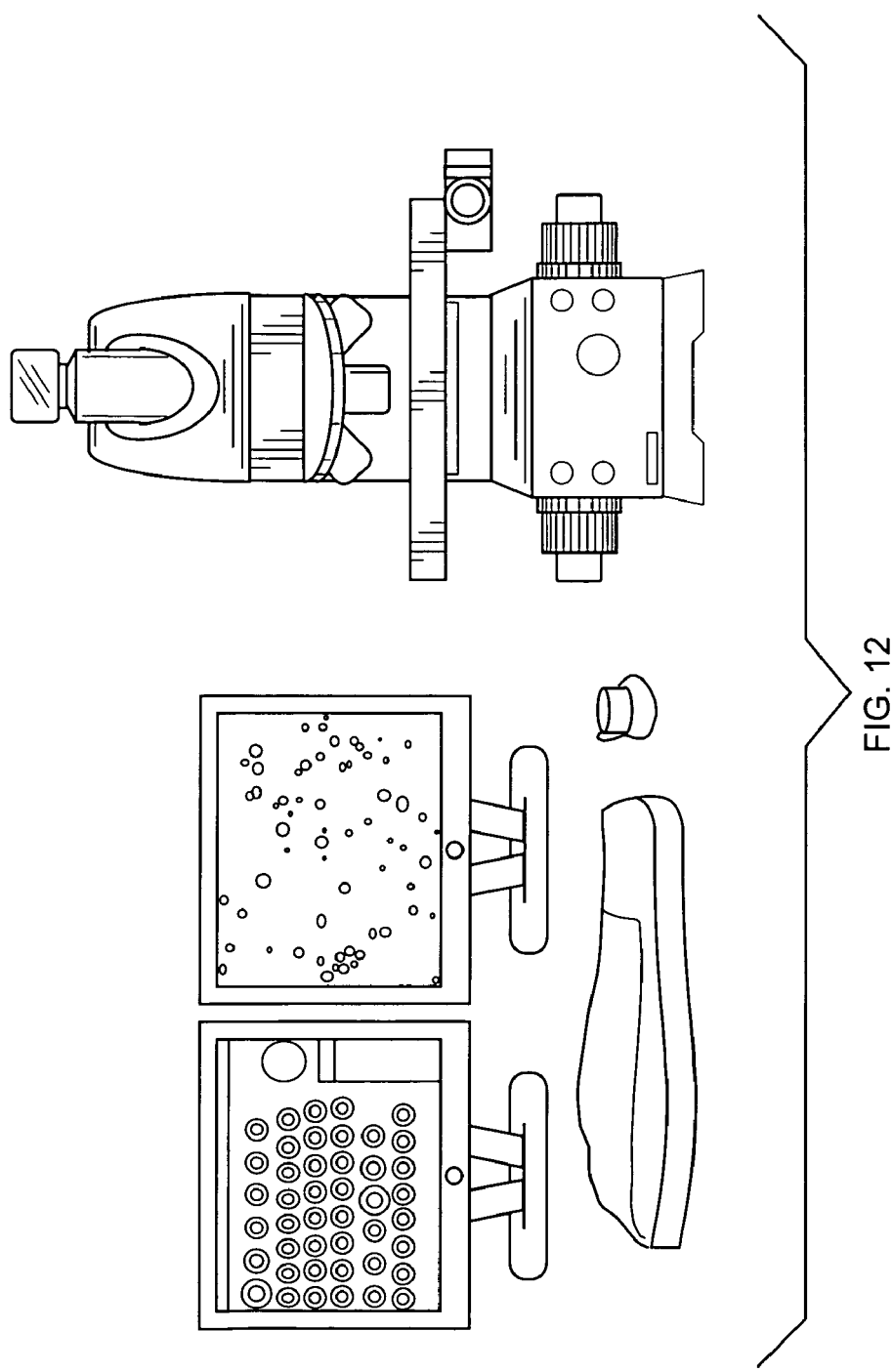
FIGS. 12-20 illustrate a particle analyzer.
Figure 13:
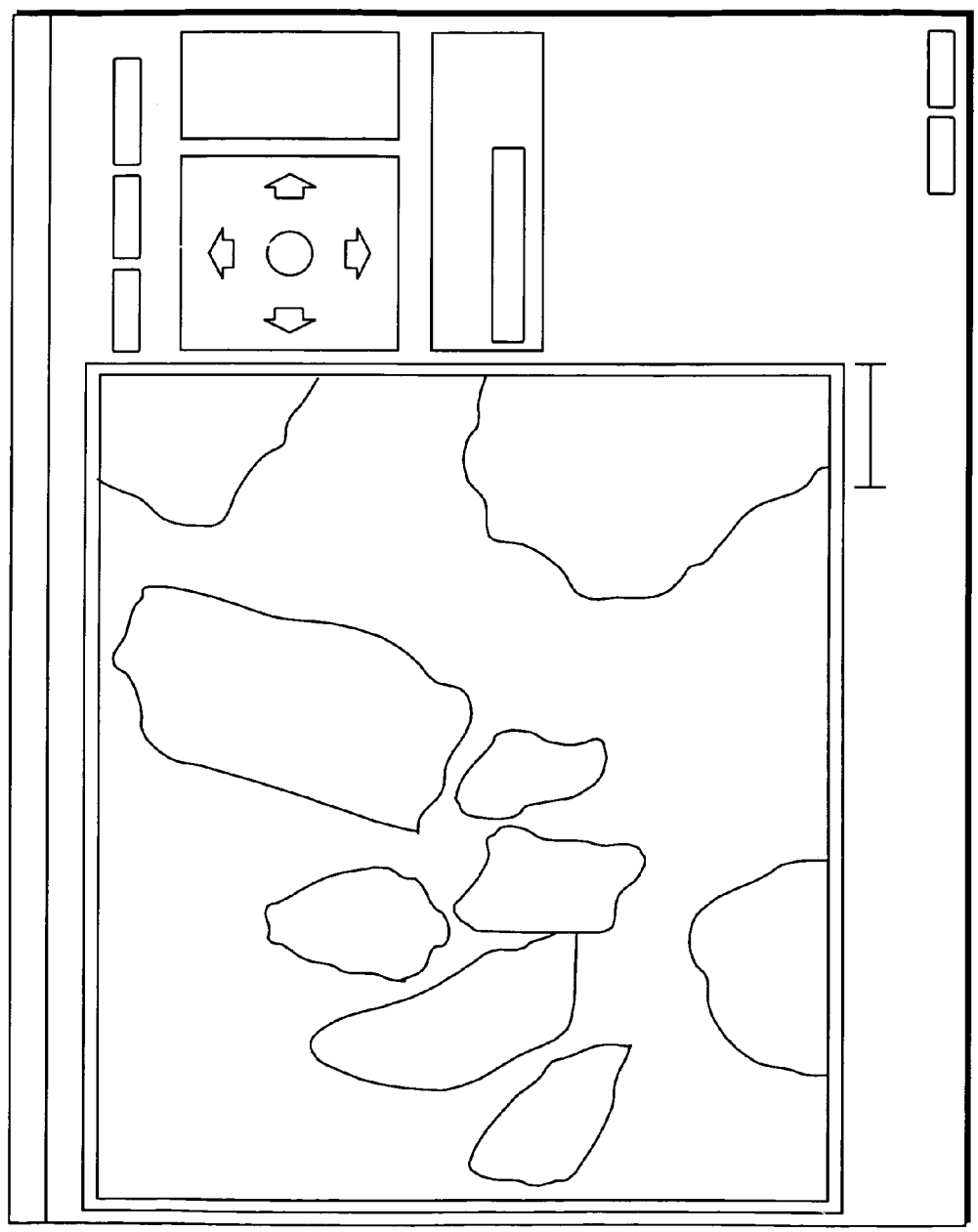
Figure 14:
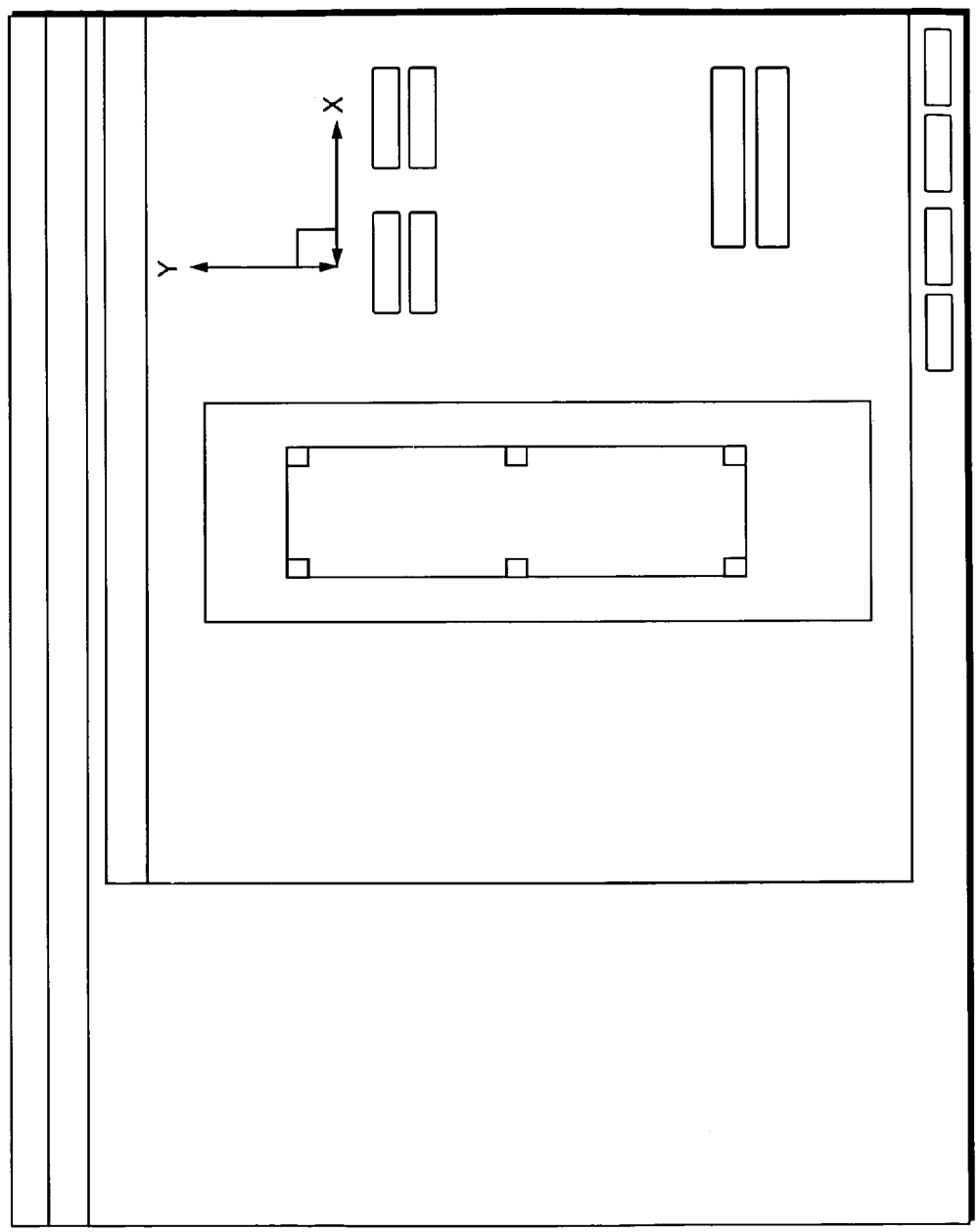
Figure 15:
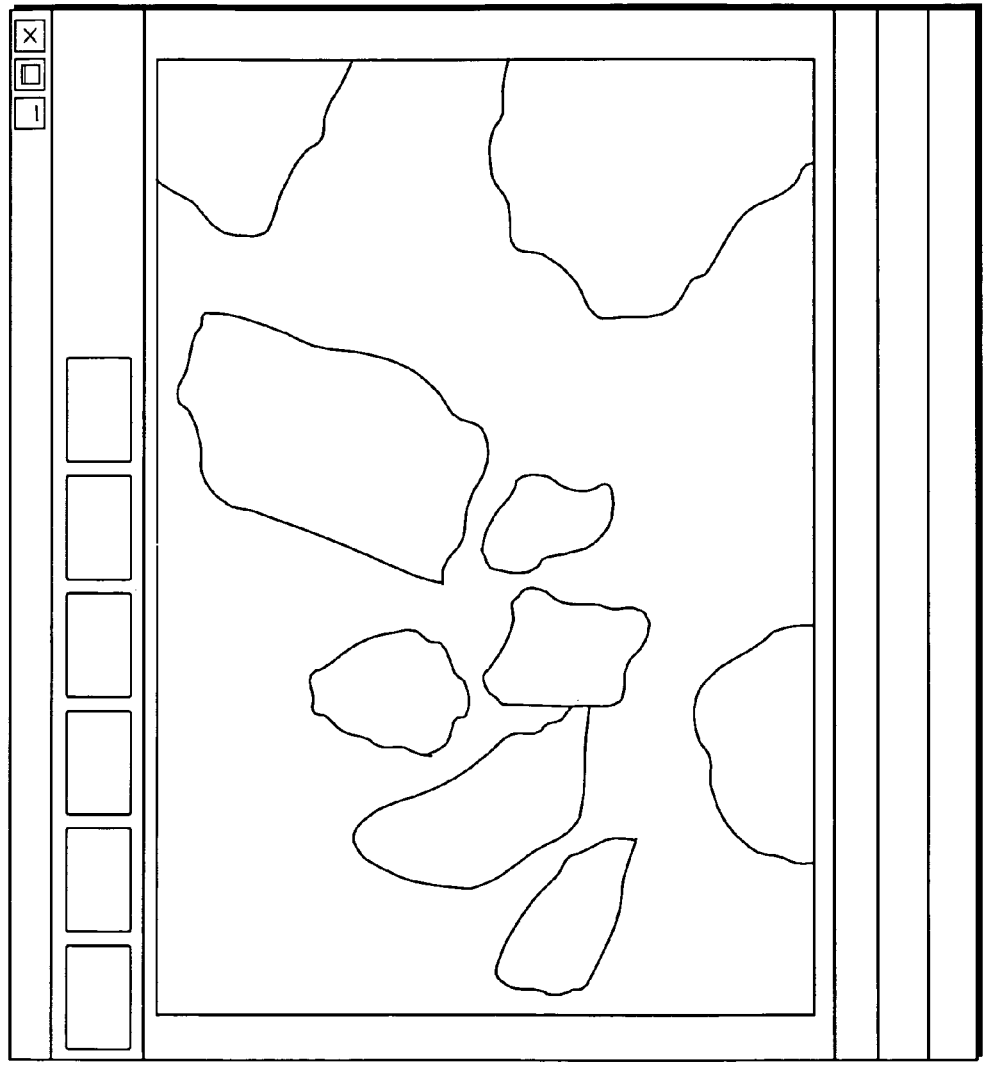
Figure 16:
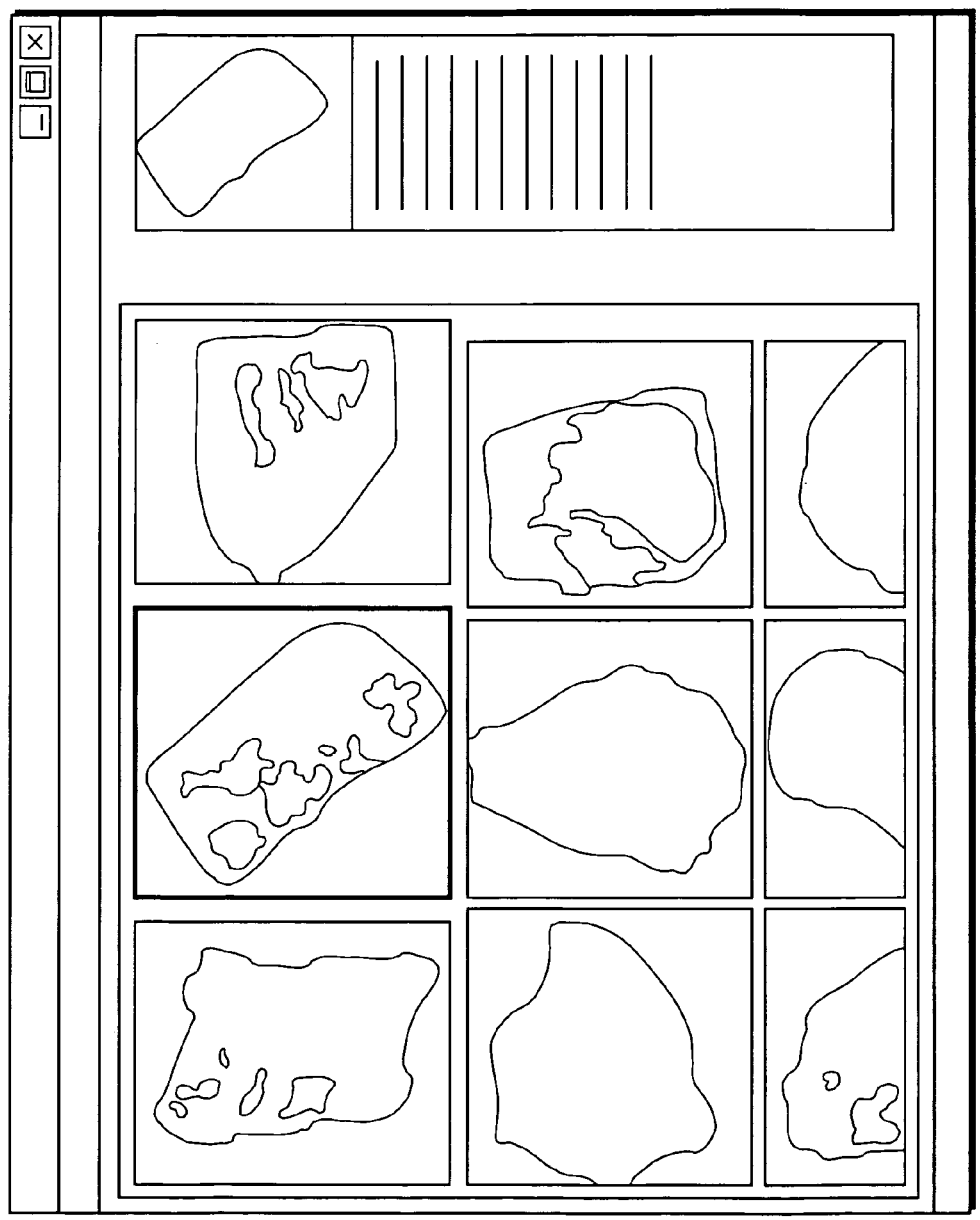
Figure 17:
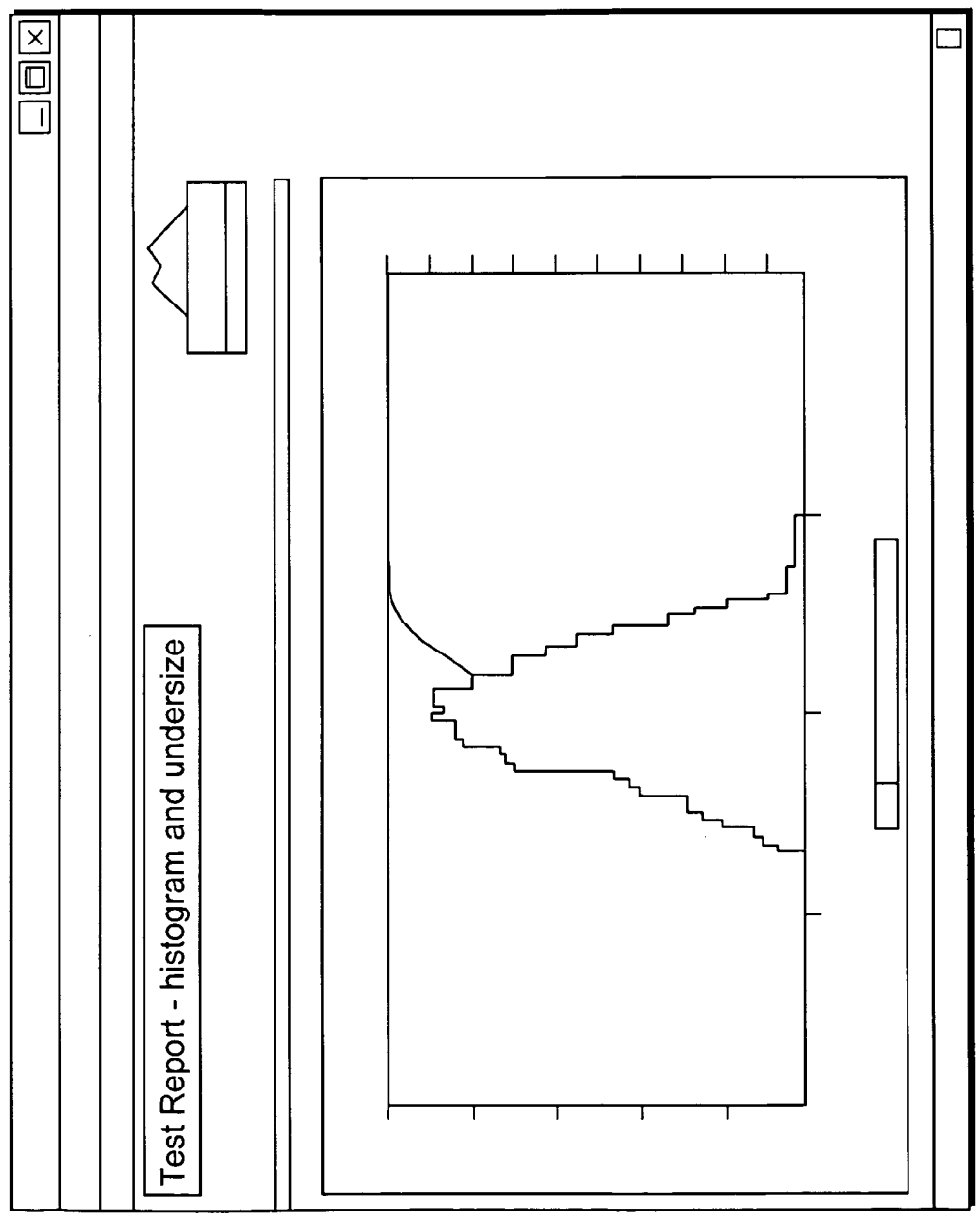

The following section describes a particle analyzer suitable for use in connection with embodiments of the invention. This analyzer is sold under the name "Morpohologi G2" by Malvern Instruments Limited of Malvern, Worcestershire UK. Referring to FIG. 12, the Morphologi G2 high sensitivity particle analyzer is more than just a microscope. It brings together the very best hardware and software in a single integrated package and provides the very highest level of automation and validation of results. It provides repeatable and routine characterization of particle size, shape and count.

The Morphologi G2 is equipped with the renowned Nikon CFI 60 optical system coupled with a high resolution digital camera for high definition aberration-free images. Microscope-quality images and statistically significant histograms offer both qualitative and quantitative information which can eliminate operator bias and saves precious man-hours. In R&D, process analysis or quality control, the Morphologi G2 delivers reliable, repeatable and validated results in minutes. It can analyze 100s of thousands of particles at the push of a button, provide particle shape and count as well as size information, record high resolution images of every particle, automatically select optics, focus and light intensity control, provide technical compliance with 21 CFR Part 11, and provide a dedicated sample preparation device. Usage of the system is illustrated Table 1, with reference to FIGS. 13-17.

TABLE 1

| Step | Description | Comments | FIG. |
|---|---|---|---|
| Method Development | Generate basic information on sample such as size range. Optimize sample dispersion conditions. | A "manual microscope" mode is available to quickly move around and view the sample in order to check basics such a dispersion quality or the approximate size rage. It employs a virtual joystick and focus, light and magnification controls. | 13 |
| Standard Operating Procedure (SOP) Creation | Optimize and select all software and hardware variables. All variables captured in a single file that can be emailed around the world. | A "wizard" assists in the generation of SOPs. A mouse-controlled scan area selection tool is available. | 14 |
| Sample Measurement | The software selects the magnification and calibrates against a grating. Light intensity and focus position are all controlled by software. | During data acquisition, status messages keep the operator informed of progress. A settings icon allows for modification of SOP settings. Quick start icon and status message bar are also provided along with a live view of the measurement frame. | 15 |
| Result Viewing/editing | View information on each individual particle or the statistics of whole distribution Sort and filter particles and create new records with certain particles excluded. | Images of all particles are recorded and can be sorted and filtered on any shape parameter and new records created with the filtered data. Particles can be sorted and filtered on any parameter. A sidebar shows a morphological parameter list for a highlighted particle. | 16 |

TABLE 1-continued

| Step | Description | Comments | FIG. |
|---|---|---|---|
| Report Creation | Display distribution, tables and result statistics. Report Designer can be used to customize the style and content of reports. | A range of reports is supplied to display distribution, tables and results statistics. The Report Designer can be used to customize the contents of these reports. Any morphological parameter can be plotted on the x-axis. The user can choose frequency, undersize, or oversize graph types, and can add specific parameters or logos or other graphics. | 17 |

Figure 18:
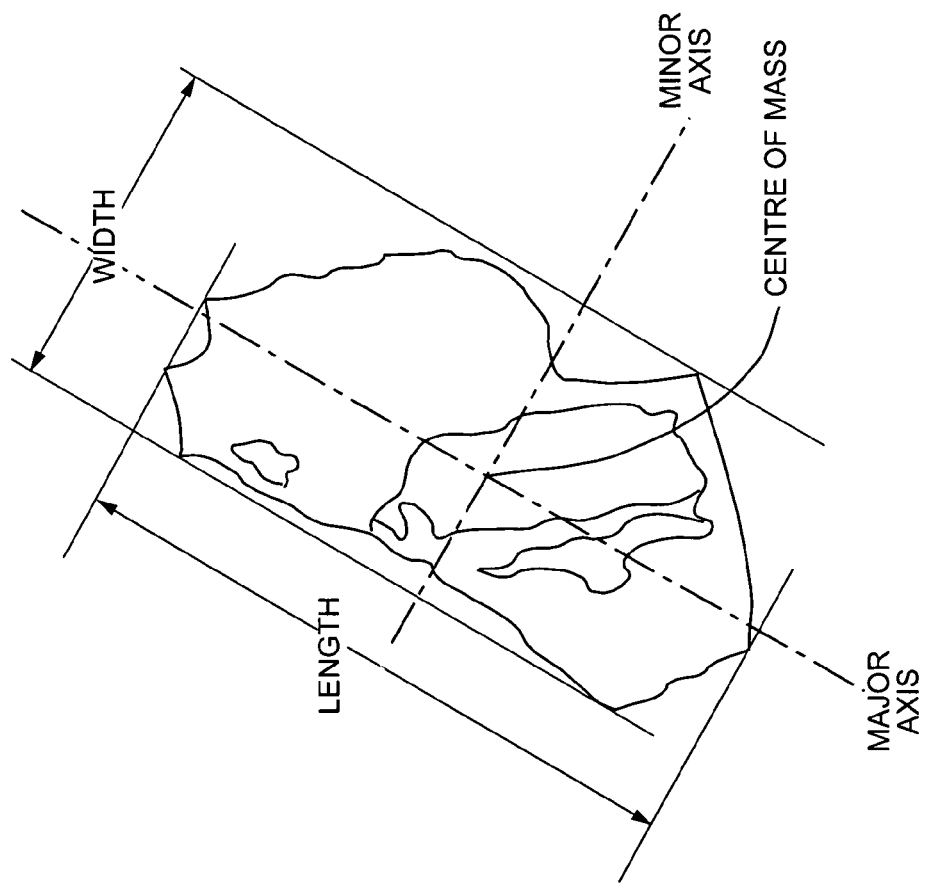

Why is Shape Analysis Important? Manual microscopy and traditional particle sizing techniques are often not sufficiently sensitive to distinguish subtle differences in raw materials. Batches of samples may differ by such a small amount that this difference is lost during the translation to a circle-equivalent or spherical-equivalent diameter. Calculating shape parameters like the ones shown in Table 2 below allow even the most subtle differences to be identified and quantified (see FIG. 18).

Figure 19:
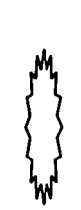

Referring to FIG. 19, shape parameters such as Circularity, Convexity and Elongation provide the user with a series of highly sensitive tools in order to identify and quantify subtle variations in particle shape and provide a "fingerprint" of each sample. Each parameter is usually normalized between 0 and 1 in order to provide quick and easy comparability. Traditional qualitative human descriptions such as "jagged", "smooth" or "needlelike" can be accurately quantified and hence correlated against important process or end-product

TABLE 2

| Parameter | Example value | Definition |
|---|---|---|
| ID | 516 | Unique ID of the particle - allocated in the order that the particles are detected |
| Magnification | 2.50 | Magnification used to make the measurement |
| CE diameter ($\mu$m) | 904.14 | The diameter of a circle with the same area as the particle |
| Length ($\mu$m) | 1306.35 | All possible lines from one point of the perimeter to another point on the perimeter are projected on the major axis (axis of minimum rotational energy). The maximum length of these projections is the length of the object. |
| Width ($\mu$m) | 678.54 | All possible lines from one point of the perimeter to another point on the perimeter are projected on the minor axis. The maximum length of these projections is the width of the object. |
| Max. Distance ($\mu$m) | 1318.07 | Largest distance between any two pixels in particle |
| Perimeter ($\mu$m) | 3619.42 | Actual perimeter of particle |
| Major axis° | 105.52 | Axis of minimum rotational energy |
| Area ($\mu$m$^2$) | 371550.78 | Actual area of particle in sq. microns |
| Area (pixels) | 215018 | Number of pixels in particle |
| Circularity | 0.785 | Circumference of equivalent area circle divided by the actual perimeter of the particle = $2\sqrt{(\pi Area)}$/Perimeter |
| HS Circularity | 0.616 | High sensitivity circularity (circularity squared) = $4\pi Area/perimeter^2$ |
| Convexity | 0.919 | Convex hull perimeter divided by actual particle perimeter |
| Solidity | 0.905 | Actual particle area divided by convex hull area |
| Aspect ratio | 0.519 | Width divided by length |
| Elongation | 0.461 | 1 - aspect ratio |
| Intensity mean | 61.310 | Average of all the greyscale values of every pixel in the particle |
| Intensity standard deviation | 29.841 | Standard deviation of all the greyscale values of every pixel in the particle |
| Center x position ($\mu$m) | 6898271.5 | x co-ordinate of center of mass of particle |
| Center y position ($\mu$m) | 1797186.3 | y coordinate of center of mass of particle | variables such as flowability, active area and grinding efficiency.

Circularity is a measure of the closeness to a perfect circle. Circularity is sensitive to both changes in overall form and surface roughness. Convexity is a measure of the surface roughness of a particle. Convexity is sensitive to changes in surface roughness but not overall form. Elongation is a measure of the length-width relationship. Elongation is unaffected by surface roughness—a smooth ellipse has a similar elongation as a apiky ellipse of smaller aspect ratio.

The Morphologi G2 includes high quality hardware to provide high quality images. It includes a high-resolution digital camera, and a motorized objective revolver that provides automatic magnification change over. It also includes a precision XY stage for sample scanning, a motorized Z axis actuator for automatic focusing, and two light sources for reflected (episcopic) and transmitted (diascopic) illumination. The system is supplied with two flat screen monitors, one for software and the other for a live video view. A range of sample holders are available to suit different samples and different sample preparation types.

The Morphologi G2 is built upon the acclaimed Nikon CFI 60 optical system which achieves both higher Numerical Apertures (NA) and longer working distances. A precision XY stage and calibration grating ensure that data is precise, secure and validated at all times. In these revolutionary optics, both axial and lateral chromatic aberration have been corrected independently in the objective and the tube lens. This geometry produces images that are crisp and clear with high contrast and minimal flare.

The precision engineered XY stage uses high accuracy, ground ball-screws to provide smooth and maintenance free motion with zero-backlash. The quiet and precise stepper motors ensure accurate positioning of the stage while the use of micro-stepping provides smooth motion at low speeds.

Precision etched chrome-on-glass gratings are built into the XY stage for calibration purposes. The gratings are certified and traceable to the National Physical Laboratory. The system automatically calibrates before every measurement to guarantee validated, secure data.

Morphologi G2 delivers the benefits listed in Table 3.

At any point in a manufacturing process from early research and development, through process-analysis, manufacturing trouble-shooting and root-cause analysis to final product quality control, this instrument provides an unprecedented level of product and process understanding. It is suitable for use in a number of areas.

The Morphologi G2 can be used for pharmaceuticals. In this application, even subtle differences in particle size or shape can significantly affect bioavailability, flowability, stability, blending and tabletting efficiency. Manufacturing processing steps including crystallization, drying, milling, blending, filtering can all introduce variability into the product and have to be precisely controlled. The extra sensitivity and resolution available in the Morphologi G2 instrument provides users with the ability to identify, measure and monitor those process variables which are critical to product quality.

Figure 20:
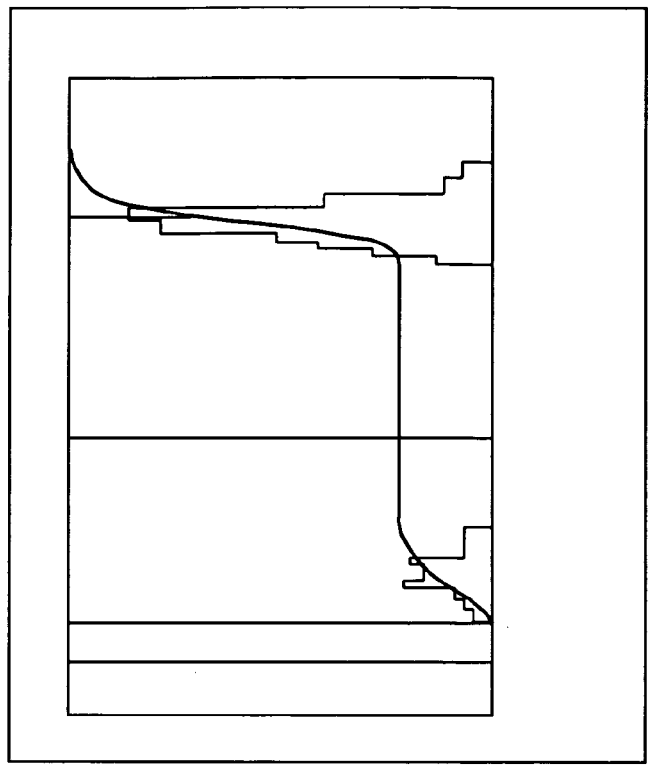
Figure 20:
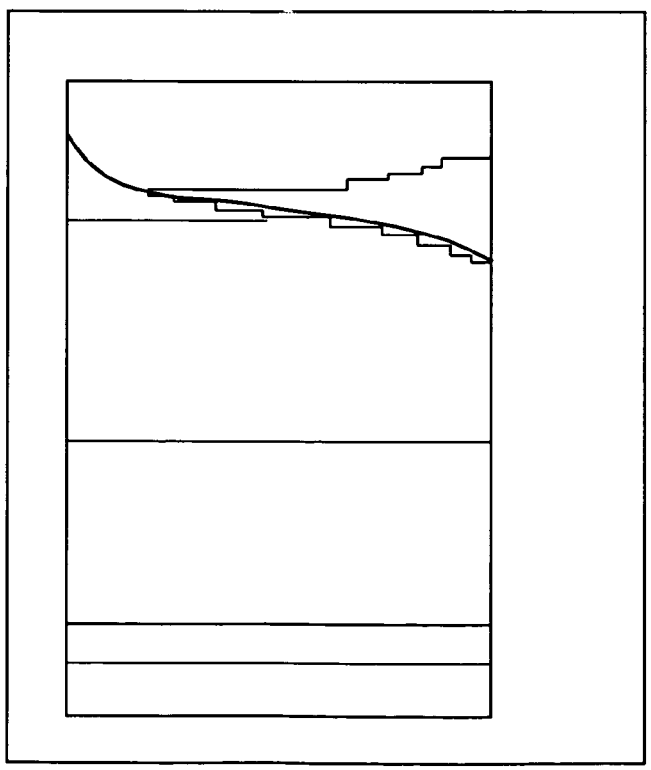

The Morphologi G2 provides high sensitivity to fine particles. Image analysis proceeds on a 'number-basis' where the contribution each particle makes to the distribution is the same—a very small particle has exactly the same weighting as a very large particle. For diagnostic or trouble-shooting purposes the presence of fines could be critical to understand any given manufacturing process (see FIG. 20).

The Morphologi G2 is also suitable for use in foreign particle detection. Image analysis is an ideal technology for detecting the presence of very small numbers of foreign particles or confirming phenomena such as agglomeration. Using single parameters or combinations of parameters, foreign particles can be detected and quantified. For example, needles or fibers can be detected using the circularity shape descriptor.

An overview of the Morphologi G2 system specifications is presented in table 4 below.

TABLE 3

| Objectives | Features |
| --- | --- |
| Repeatability and automation | The tried and tested SOP (Standard Operating Procedure) methodology records all software and hardware variables in a single file. At the click of a mouse the system selects and calibrates the required magnification, the light intensity and focus before scanning a defined area. |
| Sensitivity to shape | Particles are fully characterized by morphological parameters including circle equivalent diameter, circularity and convexity. This high quality information can be used to distinguish between materials that appear identical to a conventional microscope or traditional particle sizer. |
| High quality optics | Nikon's acclaimed CFI60 optics offer longer working distances and high N.A.s and allow high contrast imaging with a minimum of flare. |
| Statistical significance | Large numbers of particles (typically 5,000-500,000) are captured and analyzed in minutes or even seconds. |
| Images you can see | All images are saved for future reference including the x-y coordinates of each particle. If desired, one can precisely move the camera back to any position for a more detailed visual analysis. |
| Controlled orientation | To avoid errors due to random orientation, particles are dispersed onto a flat glass plate. This achieves consistency of orientation with the largest area facing the camera. |
| Regulatory compliance | The Morphologi G2 has a full validation documentation package available and provides technical compliance with the requirements of 21 CFR part 11. |

TABLE 4

| | Size, shape and count measurement of particulate samples | | | | |
|---|---|---|---|---|---|
| Size measurement | | | | | |
| Size range | 0.5 μm-1000 μm (depending upon material properties and dispersion conditions) | | | | |
| Shape measurement | Multiple shape parameters calculated for each particle and distribution generated on each parameter. Parameters include: circle equivalent diameter, Length, Width, Perimeter, Area, Aspect ratio, Circularity, Convexity, Solidity, Elongation, Intensity. | | | | |
| Optical configurations | | | | | |
| Optical system | Nikon CFI 60 Brightfield/Darkfield system | | | | |
| Magnification (at camera) | 2.5X | 5X | 10X | 20X | 50X |
| Approx. total magnification (at 17" screen) | 120X | 240X | 480X | 960X | 2400X |
| Min particle size (μm) | 20 | 10 | 5 | 3 | 0.5 |
| Max particle size (μm) | 1000 | 430 | 210 | 100 | 40 |
| Numerical aperture | 0.075 | 0.15 | 0.30 | 0.40 | 0.55 |
| Focal depth (total) (μm) | 97.78 | 24.44 | 6.11 | 3.44 | 1.82 |
| Working distance (mm) | 8.80 | 18.00 | 15.00 | 13.00 | 9.80 |
| Camera system | | | | | |
| Camera type | 1/1/8" Global shutter progressive scan CCD | | | | |
| Connection protocol type | IEEE 1 394a (Firewire ™) | | | | |
| Number of pixels | 1624 × 1236 (2 MegaPixel) | | | | |
| Pixel size | 4.4 μm × 4.4 μm | | | | |
| Sensor size | 7.15 mm × 5.44 mm | | | | |
| Minimum PC specification (Supplied with system) | DELL Mini Tower PC, Windows XP SP2, 3.0 GHz Intel Pentium IV Processor, 1 Gb RAM, 160 Gb-HDD, DVD +/− R/RW, complete with mouse, keyboard and 2 × 17" Flat Panel Monitors (1 for software and 1 for live video feed) | | | | |
| Weight and dimensions | | | | | |
| Weight (with stage fitted) | 50 kg | | | | |
| Overall dimensions (with stage fitted) | 550(w) × 850(d) × 680(h) mm | | | | |
| Suggested deskspace (with PC and 2 screens) | 850(d) × 2500(w) | | | | |
| Site requirements | | | | | |
| Power requirements | AC 100-240 V, 50-60 Hz | | | | |
| Ambient operating temp. | 10° C.-35° C. | | | | |
| Humidity | 10-90% non-condensing | | | | |
| Location | Normal laboratory conditions - out of direct sunlight | | | | |

The present invention has now been described in connection with a number of specific embodiments thereof. However, numerous modifications which are contemplated as falling within the scope of the present invention should now be apparent to those skilled in the art. It is therefore intended that the scope of the present invention be limited only by the scope of the claims appended hereto. In addition, the order of presentation of the claims should not be construed to limit the scope of any particular term in the claims.

What is claimed is:

1. A spectroscopic apparatus for investigating heterogeneity of a sample area that includes individual particles, comprising:
   an image acquisition system operative to acquire images of a plurality of individual particles in the sample area of individual particles,
   image analysis logic operative to analyze the images acquired by the image acquisition system, wherein the analysis logic includes sorting logic operative to sort the particles based on one or more of their morphological characteristics,
   a particle selection interface operatively connected to the image analysis logic and being responsive to a user selection of one or more morphological characteristics and being operative to at least semi-automatically select particles having the selected morphological characteristics,
   a spectrometer having a field of view and being operative to acquire a spectrum of at least part of one of the particles in its field of view, and
   a positioning mechanism responsive to the particle selection interface and operative to position the field of view of the spectrometer relative to the sample area based on a selection from the particle selection interface.

2. The apparatus of claim 1 wherein the positioning mechanism includes electromechanical elements.

3. The apparatus of claim 1 wherein the positioning mechanism includes an x-y stage responsive to x-y coordinate information from the particle selection interface.

4. The apparatus of claim 1 wherein the particle selection interface is responsive to direct selection of a particle by a user.

5. The apparatus of claim 1 wherein the particle selection interface is further responsive to the analysis logic to select individual particles having predetermined color characteristics.

6. The apparatus of claim 1 wherein the analysis logic includes statistical analysis logic.

7. The apparatus of claim 1 wherein the analysis logic includes contaminant detection logic.

8. The apparatus of claim 1 wherein the spectrometer is an infrared spectrometer.

9. The apparatus of claim 1 wherein the spectrometer is a Raman spectrometer.

10. The apparatus of claim 1 wherein the image acquisition system operates in the visible range.

11. The apparatus of claim 1 further including a mapping module responsive to the image acquisition system and to the spectrometer and operative to create a map that presents spectral information for each of the individual particles from the spectrometer at a location from which it was received.

12. The apparatus of claim 11 wherein the mapping module is operative to superimpose the spectral information onto an image from the image acquisition system.

13. The apparatus of claim 11 wherein the mapping module maps point measurement values to larger areas having matching physical characteristics.

14. The apparatus of claim 11 wherein the mapping module is also operative to indicate statistical properties of mapped areas.

15. The apparatus of claim 11 wherein the positioning mechanism includes electromechanical elements.

16. The apparatus of claim 11 wherein the positioning mechanism includes an x-y stage responsive to x-y coordinate information from the particle selection interface.

17. The apparatus of claim 11 wherein the particle selection interface is responsive to direct selection of a particle by a user.

18. The apparatus of claim 11 wherein the analysis logic includes statistical analysis logic.

19. The apparatus of claim 11 wherein the analysis logic includes contaminant detection logic.

20. The apparatus of claim 11 wherein the spectrometer is an infrared spectrometer.

21. The apparatus of claim 11 wherein the spectrometer is a Raman spectrometer.

22. The apparatus of claim 11 wherein the image acquisition system operates in the visible range.

23. The apparatus of claim 1 further including a display and display logic responsive to the image acquisition system and operative to present to the user on the display a plurality of images of ones of the individual particles.

24. The apparatus of claim 23 wherein the particle selection interface is responsive to direct selection of one of the displayed particles by a user.

25. A spectroscopic method for investigating heterogeneity of a sample area that includes individual particles, comprising:
acquiring images of a plurality of individual particles in the sample area using an image acquisition system,
analyzing the images acquired by the image acquisition system using analysis logic,
receiving a user selection of one or more morphological characteristics,
at least semi-automatically selecting of one of the individual particles for which an image has been obtained based on results of the step of analyzing, wherein the step of selecting is operative to sort the particles based on one or more of their morphological characteristics based on a selection from the user,
positioning a field of view of a spectrometer relative to the sample area so as to place at least part of the selected particle in the field of view, and
acquiring a spectrum of the selected particle.

26. The method of claim 23 further including the step of mapping spectral information from the spectrometer to a location from which it was received.

27. The method of claim 23 further including the steps of deriving physical information about the one of the individual particles, and setting a spectral range of the step of acquiring in response to the physical information.

28. The method of claim 23 wherein the steps of acquiring images, analyzing, selecting, positioning, and acquiring a spectrum are performed for a pharmaceutical formulation.

29. A spectroscopic apparatus for investigating heterogeneity of a sample area that includes individual particles, comprising:
means for acquiring images of a plurality of individual particles in a sample,
means for analyzing the images acquired by the means for acquiring,
means for receiving a user selection of one or more morphological characteristics,
means responsive to the means for receiving a user selection for at least semi-automatically selecting of one of the individual particles for which an image has been obtained based on results from the means for analyzing,
means for positioning a field of view of a spectrometer relative to the sample area so as to place at least part of the selected particle in the field of view, and
means for acquiring a spectrum of the selected particle.

* * * * *